United States Patent [19]

Hjerten

[11] Patent Number: 4,911,808

[45] Date of Patent: Mar. 27, 1990

[54] MOBILIZATION OF FOCUSED PROTEIN ZONES BY ION INTRODUCTION

[75] Inventor: Stellan Hjerten, Uppsala, Sweden

[73] Assignee: Bio-Rad Laboratories, Inc., Hercules, Calif.

[21] Appl. No.: 259,231

[22] Filed: Oct. 18, 1988

Related U.S. Application Data

[63] Continuation-in-part of Ser. No. 903,634, Sep. 4, 1986, abandoned.

[51] Int. Cl.$^4$ ..................... G01N 27/26; B01D 57/02
[52] U.S. Cl. ............................ 204/182.9; 204/183.2
[58] Field of Search ........................... 204/182.9, 183.2

[56] References Cited

PUBLICATIONS

McCormick, A. et al., "Selective Elution of Zones from Preparative Isoelectric Focusing Gels by Ampholytes and Buffers" *Analytical Biochemistry* 75, 314–324 (1976).
McCormick, A. et al., "Preparative Separation of Hemoglobins A and S by Gel Electrofocusing, Using Selective Zone Elution by Gel Transposition between Suitable Anolytes and Catholytes" *Analytical Biochemistry* 85, 209–218 (1978).

*Primary Examiner*—John F. Niebling
*Assistant Examiner*—John S. Starsiak, Jr.
*Attorney, Agent, or Firm*—Townsend and Townsend

[57] ABSTRACT

Zones of ampholytic substances which have been isoelectrically focused in a separation medium are mobilized for analytical or preparative purposes by either introducing anions other than hydroxyl ions to the separation medium toward the catholyte end or adding cations other than protons to the separation medium toward the anolyte end to produce a pH shift in the separation medium, thus restoring a charge to the focused ampholytes so that they will mobilize under the influence of a voltage applied across the medium. In preferred embodiments, the anion or cation introduction is achieved by supplementing the catholyte or anolyte, respectfully, with a strong electrolyte and permitting the cations or anions to migrate into the separation medium under the influence of the electric field. Detection is achieved by permitting the focused zones to migrate past a fixed point in the separation medium. Alternatively, detection of the zones outside of the separation medium and/or recovery of the individual proteins themselves may be achieved in the same way provided the receiving electrolyte has an appropriate pH which will permit migration of the zones to continue into the electrolyte itself.

15 Claims, 1 Drawing Sheet

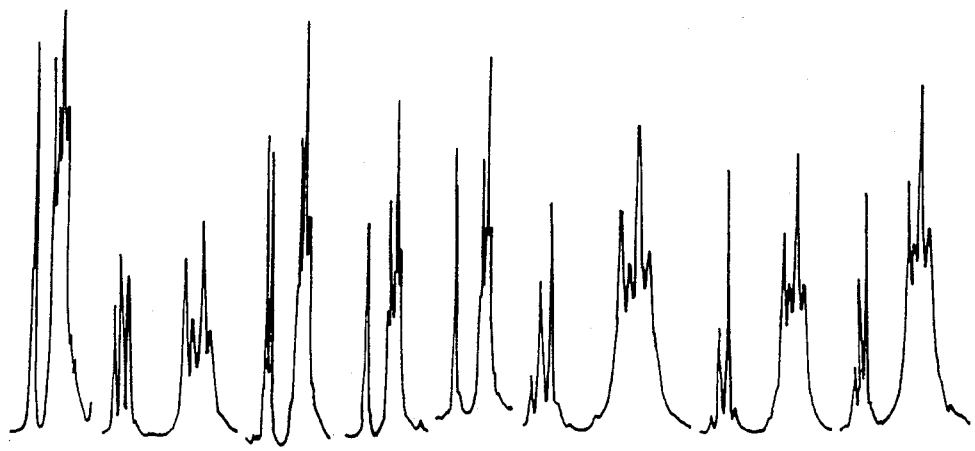
FIG._1.  FIG._2.  FIG._3.  FIG._4. FIG._5.  FIG._6.  FIG._7.  FIG._8.
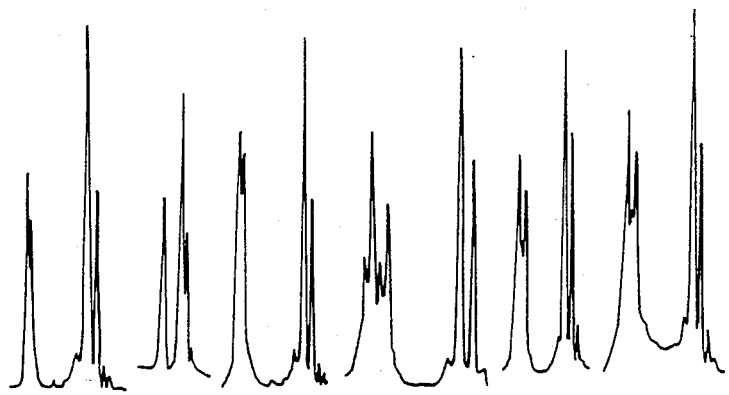
FIG._9.  FIG._10. FIG._11.  FIG._12.  FIG._13.  FIG._14.

MOBILIZATION OF FOCUSED PROTEIN ZONES BY ION INTRODUCTION

CROSS REFERENCE TO RELATED APPLICATION

This application is a continuation-in-part of application Ser. No. 06/903,634, filed Sept. 4, 1986, now abandoned.

BACKGROUND OF THE INVENTION

This invention relates to isoelectric focusing, and particularly to methods for mobilizing a focused pattern of ampholytes such as, for instance, proteins in a separation medium for purposes of recovery, detection or both.

High performance liquid chromatography (HPLC) is popular for both analytical and small scale preparative purposes, due to its ability to provide both high speed and high resolution of very small samples. Electrophoresis, including isoelectric focusing, may also be done on a small scale, with similar advantages of speed and resolution.

To achieve speeds similar to those obtainable in HPLC systems, electrophoresis-based systems must use detection techniques which avoid staining and derivatization. The most suitable techniques are light absorption measurements, done either by scanning the medium in which the zones are focused, or by mobilizing the focused zones past a single detection point in the medium itself or out of the medium into a detection cuvette.

Mobilization has the advantage of not requiring motorized scanning equipment. It further enables one to recover the isolated zones individually for preparative purposes. Mobilization by pumping a solution through the tube or other vessel in which the medium is held to purge the vessel by hydrodynamic flow has previously been used following isoelectric focusing in sucrose gradients (without voltage applied). In this case, the parabolic zone distortion caused by the pumping is suppressed by the sucrose gradient, although zone broadening by diffusion still occurs. This way of suppressing zone distortion only works when the column has a relatively large diameter, for instance 3–20 mm, and only when it is mounted in a vertical position. For narrow-bore columns (diameters in the range 0.05–2 mm) sucrose gradients will not suppress the parabolic zone distortion occurring during the pumping procedure. Mobilization of isoelectrically focused zones by pumping cannot, of course, be used when the focusing is performed in a gel.

U.S. patent application Ser. No. 06/787,291, filed Oct. 15, 1985, commonly owned and copending herewith, discloses a mobilization method consisting of changing the pH of either the anolyte or the catholyte or both after the focusing step to provide both anolyte and catholyte with pH's varying in the same direction from the isoelectric points of each of the ampholyte zones focused in the separation medium. The voltage which is then applied across the medium causes the entire protein zone pattern to move as a unit out of the medium. The preferred embodiment in the disclosure involved replacing the anolyte used in the focusing step with the catholyte, or vice versa, with the result that the same solution was in contact with both ends of the separation medium.

SUMMARY OF THE INVENTION

It has now been discovered that mobilization may be achieved by introducing anions other than hydroxyl ions or cations other than protons to the separation medium at the catholyte or anolyte end, respectfully. The ions thus introduced produce a shift in the proton (and hydroxyl ion) concentration in the immediate region due to the tendency of the medium to maintain its electroneutrality. The pH in the regions where these ions are introduced thus shifts so that all ampholytes become charged once again, and start migrating. The method of the present invention thus produces a change in the pH of the separation medium directly and independently of the pH's of the anolyte and catholyte.

The invention may be used for mobilization of the ampholyte zones past a fixed point in the separation medium (for detection at that point), or for mobilization of the ampholyte zones out of the medium entirely for detection at an external point and/or recovery of the individual ampholytes. Mobilization of the zones outside of the medium is achieved by appropriate adjustment of the pH of the electrode solution toward which the mobilization is directed.

BRIEF DESCRIPTION OF THE DRAWINGS

The fourteen figures attached hereto are strip-chart recorder traces from an ultraviolet absorption detector, representing the separation of human hemoglobin from human transferrin.

FIGS. 1 and 9 are traces generated by prior art techniques while

FIGS. 2 to 8 and 10 to 14 represent various embodiments of the present invention.

DETAILED DESCRIPTION OF THE INVENTION

In accordance with the present invention, ions are introduced into the separation medium at either one end or the other, the ions being of appropriate polarity to cause a shift in either the proton or hydroxyl ion concentration so that the pH of the entire medium is either above or below the isoelectric points of all ampholyte zones focused in the medium. The proton or hydroxyl ion shift occurs as a result of the tendency of the ampholytic separation medium to maintain its electroneutrality. Cations are introduced into the anolyte when the mobilization is to take place toward the anode; and anions are introduced into the catholyte when the mobilization is to take place toward the cathode. The result of the ionic shift will then be to raise the pH or lower it in its entirety so that the pH at all points in the separation medium will be either above or below the isoelectric points of all of the ampholyte zones and the ampholytes focused in these zones will all be charged. When the voltage is then applied, the focused ampholyte will migrate toward one end or the other of the separation medium, i.e., in either the anodic or the cathodic direction. Thus, cations other than protons are added at the anolyte end to raise the pH, or anions other than hydroxyl ions are added at the catholyte end to lower the pH. Examples of such cations are alkali metal and alkaline earth metal ions. Examples of such anions are halide, sulfate, phosphate and acetate ions.

The introduction of ions is achieved by adding a strong electrolyte to the anolyte or catholyte, the strong electrolyte dissociating upon dissolving to release the ions of interest. The term "strong electrolyte" is used in this specification as it is used among those skilled in the art, and refers to species which are highly dissociated in solutions even at moderate dilutions, and which do not obey Ostwald's Law. This is as opposed, for example, to partially dissociated species such as buffers, whose degree of dissociation is affected by and varies with pH. Strong electrolytes may generally be thought of as those with pK values of less than about $-1$, preferably less than about $-3$.

An effective way of creating a pH gradient is to introduce the electrolyte into the anolyte or catholyte and permit electrophoretic migration of the ions from the anolyte or catholyte into the separation medium. For example, an anolyte- or catholyte-soluble salt which is dissociable into anions and cations may be introduced into the anolyte or catholyte solution. When the electric potential is applied between the anolyte and catholyte, the appropriate ion will selectively migrate into the separation medium, providing the pH shift in the medium.

Separation media to which the present invention is applicable include all media in which ampholytes such as, for example, proteins, peptides and bacteria can move under the influence of an electric field and can be focused in discrete zones by isoelectric focusing. Such media may include liquids, gels and suspensions. Liquid media are generally preferred. The pH gradient is created by an appropriately selected electrolyte, preferably an ampholyte, to promote the focusing. The ampholyte used as the separation medium will be referred to herein as the "carrier ampholyte" to distinguish it from the ampholyte in the sample to be separated.

The carrier ampholyte may be supplemented with an additive to suppress protein precipitation. Examples are ethylene glycol (10-50% by volume). G3707 (0.5-2% by volume, a detergent available from Atlas Chemicals, Everberg, Belgium) and Brij 35 (0.5-2% by volume, a polyoxyethylene lauryl ether available from Nutritional Biochemicals Corp., Cleveland, Ohio).

The separation medium may assume any physical configuration which will permit the separation of sample ampholytes (proteins) into zones along a single longitudinal axis. Preferred configurations will be those which avoid the accumulation of heat generated by the electrical current, so as to minimize the distortion of the zones during both focusing and mobilization. Thin-walled, thin diameter capillary tubes are preferred, particularly when on-line detection is used. Particularly useful are glass tubes whose inner walls have been coated to eliminate zone distortion due to electroendosmosis and the adsorption of solutes by the glass wall. Methyl cellulose and non-crosslinked polyacrylamide are examples of coatings which provide this effect.

The isoelectric focusing which precedes the mobilization may be done according to conventional methods, involving the combination of an electric field and a pH gradient. The pH gradient preferably runs from an anolyte which is acid or neutral to a catholyte which is neutral or basic. In particularly preferred embodiments, the anolyte is an acidic aqueous solution and the catholyte is a basic aqueous solution. Isoelectric focusing is continued until a steady state is achieved—i.e., until movement of ampholytes in the separation medium is substantially stopped.

Once the focusing is complete, the appropriate ions are introduced into the separation medium by voltage applied across the separation medium. The entire pattern of focused ampholyte zones moves within the medium in a direction dictated by the net charge on the focused ampholytes. The voltage may be adjusted during the mobilization so that the zones travel with a minimum of distortion from their steady state forms and relative positions. Thus, conditions are adjusted as necessary to approach as closely as possible a purely linear translational motion of the protein zone pattern with respect to the stationary separation medium.

If there is no change in the pH's of the anolyte and catholyte themselves between the focusing and mobilization stages, the ampholytes will cease moving once they reach the end of the separation chamber since the pH at that point will be close to that of the anolyte or catholyte with which that end is in contact, and therefore below or above (respectively) the isoelectric points of the ampholytes. This is acceptable when one merely seeks to perform zone detection at a fixed point in the separation medium itself (i.e, on-tube detection). When external detection is desired, or when recovery of individual ampholytes for preparative purposes is desired, the protein zones may be moved out of the separation medium by changing the pH of the receiving anolyte (catholyte) to be higher (lower) than the most extreme isoelectric point among the ampholytes focused in the medium.

The following examples are offered for illustrative purposes only, and are intended neither to define or limit the invention in any manner.

EXAMPLES

A glass tube measuring 110 mm in length and having an inner diameter of 0.05 mm and a wall thickness of 0.05 mm was coated with non-crosslinked polyaclylamide in order to eliminate electroendosmosis and adsorption of proteins onto the tube wall. The tube was then filled with a 2.5% (volume basis) solution of Pharmalyte TM (a carrier ampholyte obtained from Pharmacia Fine Chemicals, Uppsala, Sweden), pH 3-10, containing human transferring (5 micrograms/microliter) obtained from KABI/Vitrum, Stockholm, Sweden, and human hemoglobin (5 micrograms/microliter) prepared from outdated blood. The tube was then placed in an isoelectric focusing apparatus using 0.02M phosphoric acid as the anolyte and 0.02M sodium hydroxide as the catholyte. An agarose gel plug was inserted in the cathodic end of the tube. For detection, a prism monochromator focused a narrow beam having a wavelength of 280 nm across a segment of the tube near one end. A photomultiplier was arranged to intercept the beam after passing through the tube. Its output was recorded on a strip-chart recorder.

Focusing was achieved by applying a voltage of 3000 volts across the tube for six minutes. During this time the current decreased from 15 microamps to 1 microamp.

For comparison purposes, mobilization was then achieved according to the technique disclosed in commonly owned co-pending application Ser. No. 06/787,291, filed Oct. 15, 1985, by exchanging the 0.02M phosphoric acid in the anolyte chamber for 0.02M sodium hydroxide sd that both anolyte and catholyte were the same sodium hydroxide solution. A voltage of 4000 volts was applied for about fifteen minutes during which time the current rose from 2 to 200 microamps. The recorder output is shown in FIG. 1. To illustrate the present invention, the experiment was repeated several times in which mobilization was achieved by using a variety of solutions in place of the 0.02M sodium hydroxide as substitutes for the phosphoric acid in the anolyte, and in some cases modifying the catholyte as well. The solutions used are listed in Table 1 together with those for the comparison run (FIG. 1), and the results are shown in the figures indicated:

TABLE 1

MOBILIZATION CONDITIONS

| | Anolyte | Catholyte | Migration Direction |
|---|---|---|---|
| FIG. 1 | 0.02 M NaOH | 0.02 M NaOH | anodic |
| FIG. 2 | 0.02 M $H_3PO_4$ + 0.08 M NaCl | 0.02 M NaOH | anodic |
| FIG. 3 | 0.02 M sodium phosphate, pH 3.6 | 0.02 M NaOH | anodic |
| FIG. 4 | 0.02 M sodium phosphate, pH 6.8 | 0.02 M NaOH | anodic |
| FIG. 5 | 0.02 M sodium phosphate, pH 11.5 | 0.02 M NaOH | anodic |
| FIG. 6 | 0.02 M ethanolamine, pH 11 | 0.02 M NaOH | anodic |
| FIG. 7 | 0.02 M sodium phosphate, pH 6.8 | 0.02 M glycine, pH 9.0 with NaOH | anodic |
| FIG. 8 | 0.02 M NaCl | 0.02 M glycine, pH 9.0 with NaOH | anodic |

The hemoglobin used in the runs represented by FIGS. 2, 3, 4 and 5 was obtained from a separate batch, and as a result the isoelectric focusing pattern for these runs appears somewhat different from the rest. Nevertheless, the presence of a trace in each figure indicates that mobilization occurred in each run.

In the FIG. 2 run, the only change introduced to effect mobilization was the addition of NaCl to the anolyte; no change in pH was made. FIGS. 3 through 5 demonstrate that mobilization can be achieved by sodium ion migration regardless of the pH of the anolyte. FIG. 6 demonstrates the effective use of the ethanolammonium cation as a substitute for the sodium cation. FIG. 7 demonstrates the combination of sodium ion migration in accordance with a possible isotachophoretic mobilization, using phosphate as the leading ion and glycine as the terminating ion, and FIG. 8 demonstrates the use of NaCl only in the anolyte.

A second set of runs was performed to demonstrate mobilization in the cathodic direction. As before, a comparison run was done first according to the technique disclosed in the above-referenced application Ser. No. 06/787,291, this time however exchanging the 0.02M sodium hydroxide in the catholyte chamber for 0.02M phosphoric acid after focusing had been completed. The remaining conditions were the same. The resulting recorder trace is shown in FIG. 9.

The experiment was then repeated using various catholyte substitutes in place of the 0.02M phosphoric acid for the mobilization step. The solutions used are listed in Table 2 together with those for the comparison run (FIG. 9), and the results are shown in the figures indicated:

TABLE 2

MOBILIZATION CONDITIONS

| | Anolyte | Catholyte | Migration Direction |
|---|---|---|---|
| FIG. 9 | 0.02 M $H_3PO_4$ | 0.2 M $H_3PO_4$ | cathodic |
| FIG. 10 | 0.02 M $H_3PO_4$ | 0.1 M NaCl | cathodic |
| FIG. 11 | 0.02 M $H_3PO_4$ | 0.02 M sodium phosphate, pH 6.8 | cathodic |
| FIG. 12 | 0.02 M $H_3PO_4$ | 0.02 M NaOH + 0.02 M NaCl | cathodic |
| FIG. 13 | 0.02 M $H_3PO_4$ | 0.02 M NaOH + 0.04 M NaCl | cathodic |
| FIG. 14 | 0.02 M $H_3PO_4$ | 0.02 M NaOH + 0.08 M NaCl | cathodic |

These figures demonstrate that mobilization is achieved by phosphate and chloride ions regardless of the pH of the catholyte and over a range of chloride ion concentration. The foregoing is offered primarily for purposes of illustration. It will be readily apparent to those skilled in the art that modifications and variations of the materials and/or procedures described herein may be introduced with successful results without departing from the spirit and scope of the invention.

What is claimed is:

1. A method for the mobilization of zones of ampholyte substances isoelectrically focused in an ampholytic separation medium having a first end in contact with an anolyte and a second end in contact with a catholyte differing in pH from said anolyte by a pH differential, said method comprising:
   (a) introducing a strong electrolyte into said separation medium at one end selected from said first and second ends, said strong electrolyte upon dissociation releasing ions other than $H^+$ and $OH^-$, the sign of said ions being positive when introduced into the anolyte and negative when introduced into the catholyte, until the pH's at all points in said separation medium vary in the same direction from the isoelectric points of each of said zones: and
   (b) applying a voltage between said anolyte and said catholyte of sufficient intensity to mobilize said zones with respect to said separation medium.

2. A method in accordance with claim 1 in which said selected end is said first end and step (a) comprises introducing said strong electrolyte to said first end only.

3. A method in accordance with claim 2 in which step (a) comprises introducing said strong electrolyte to said anolyte, thereby releasing therein cations other than $H^+$, and permitting said cations so released to migrate from said anolyte into said separation medium.

4. A method in accordance with claim 1 in which said selected end is said second end and step (a) comprises introducing said strong electrolyte to said second end only.

5. A method in accordance with claim 4 in which step (a) comprises introducing said strong electrolyte to said catholyte, thereby releasing therein anions other than $OH^-$, and permitting said anions so released to migrate from said catholyte into said separation medium.

6. A method in accordance with claim 1 in which said strong electrolyte is an anolyte-soluble salt, and step (a) comprises adding said anolyte-soluble salt to said anolyte and permitting the cations thereof to migrate into said separation medium.

7. A method in accordance with claim 1 in which said strong electrolyte is a catholyte-soluble salt, and step (a) comprises adding said catholyte-soluble salt to said catholyte and permitting the anions thereof to migrate into said separation medium.

8. A method in accordance with claim 6 in which said anolyte-soluble salt is a member selected from the group consisting of alkali metal and alkaline earth metal halides.

9. A method in accordance with claim 7 in which said catholyte-soluble salt is a member selected from the group consisting of alkali metal and alkaline earth metal halides.

10. A method in accordance with claim 3 in which said cations are selected from the group consisting of alkali metal and alkaline earth metal ions.

11. A method in accordance with claim 5 in which said anions are selected from the group consisting of halide, sulfate, phosphate and acetate ions.

12. A method in accordance with claim 1 in which the voltage of step (b) is of the same polarity as that under which said zones have been isoelectrically focused.

13. A method in accordance with claim 1 in which the voltage of step (b) is of the same polarity as and at least as great as that under which said zones have been isoelectrically focused.

14. A method for the mobilization of zones isoelectrically focused in an ampholytic separation medium having a first end in contact with an anolyte and a second end in contact with a catholyte differing in pH from said anolyte, said method comprising:
 (a) adding to a member selected from said anolyte and said catholyte a strong electrolyte comprising a salt dissociable therein into ions and permitting the migration into said separation medium of those of said ions whose sign is positive when introduced into the anolyte and negative when introduced into the catholyte, to provide pH's at all points in said separation medium with values varying in the same direction from the isoelectric points of each of said zones; and
 (b) applying a voltage between said anolyte and said catholyte of sufficient intensity to mobilize said zones with respect to said separation medium, said voltage being of the same polarity as and at least as great as that under which said zones have been isoelectrically focused.

15. A method in accordance with claim 1 further comprising changing at least one member selected from said anolyte and said catholyte to provide said anolyte and said catholyte with pH's varying in the same direction from the isoelectric points of each of said zones as the pH's at all points in said separation medium in step (a).

* * * * *